United States Patent
Beltran et al.

(10) Patent No.: US 11,779,826 B2
(45) Date of Patent: *Oct. 10, 2023

(54) MULTI-PHASE SWITCHED-MODE POWER SUPPLIES

(71) Applicant: Astec International Limited, Kowloon (HK)

(72) Inventors: Israel Gomez Beltran, Antipolo (PH); Zhizhi Li, Kwun Tong (HK); Siu Lun Wu, Hong Kong (HK)

(73) Assignee: Astec International Limited, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,378

(22) Filed: Jun. 8, 2022

(65) Prior Publication Data

US 2022/0387872 A1 Dec. 8, 2022

Related U.S. Application Data

(63) Continuation of application No. 17/007,862, filed on Aug. 31, 2020, now Pat. No. 11,264,908.

(51) Int. Cl.
*H02M 3/158* (2006.01)
*A63B 71/06* (2006.01)
(Continued)

(52) U.S. Cl.
CPC ...... *A63B 71/0622* (2013.01); *A63B 24/0062* (2013.01); *G06F 3/015* (2013.01);
(Continued)

(58) Field of Classification Search
CPC ............. H02M 1/0043; H02M 1/4216; H02M 1/4225; H02M 3/1584; H02M 3/1586; H02M 1/4291
See application file for complete search history.

(56) References Cited

U.S. PATENT DOCUMENTS

| | | |
|---|---|---|
| 5,905,369 A | 5/1999 | Ishii et al. |
| 7,116,087 B2 | 10/2006 | Zhang et al. |

(Continued)

FOREIGN PATENT DOCUMENTS

| | | |
|---|---|---|
| CN | 102655372 B | 5/2016 |
| CN | 103563232 B | 6/2016 |

(Continued)

OTHER PUBLICATIONS

European Office Action for EP Application No. 21190243.2, dated Dec. 12, 2022; 6 pages.

(Continued)

*Primary Examiner* — Adolf D Berhane

(57) ABSTRACT

A multi-phase switched-mode power supply includes first and second interleaved phase circuits coupled between input and output terminals. The first phase circuit includes a first inductor coupled with a first switch, and the second phase circuit includes a second inductor coupled with a second switch. A control circuit is configured to output first and second PWM signals to the first and second switches. An on time of the second PWM signal is equal to an on time of the first PWM signal plus a fixed offset time period. The control circuit is configured to determine a period between rising edges of the first PWM signal in order to determine an off trigger PWM signal, and change the second PWM signal to a logical low value when a falling edge of the off trigger PWM signal occurs while the second PWM signal has a logical high value.

20 Claims, 9 Drawing Sheets

(51) Int. Cl.
  *G16H 20/30* (2018.01)
  *G06F 3/01* (2006.01)
  *A63B 24/00* (2006.01)
  *H02M 1/42* (2007.01)
  *H02M 1/00* (2006.01)

(52) U.S. Cl.
  CPC .......... *G16H 20/30* (2018.01); *H02M 1/0043* (2021.05); *H02M 1/4216* (2013.01); *H02M 1/4225* (2013.01); *H02M 3/1584* (2013.01); *G06F 2218/12* (2023.01); *H02M 1/4291* (2021.05); *H02M 3/1586* (2021.05)

(56) References Cited

U.S. PATENT DOCUMENTS

| | | | |
|---|---|---|---|
| 8,325,004 | B2 | 12/2012 | Nagano et al. |
| 10,395,819 | B2 | 8/2019 | Wukovits et al. |
| 10,992,230 | B1 | 4/2021 | Arcudia |
| 11,108,329 | B1 | 8/2021 | Sigamani |
| 11,264,908 | B1 * | 3/2022 | Beltran ............... H02M 1/0009 |
| 2007/0253223 | A1 | 11/2007 | Neidorff et al. |
| 2007/0253224 | A1 | 11/2007 | Cohen et al. |
| 2014/0334196 | A1 | 11/2014 | Chen et al. |
| 2018/0061560 | A1 | 3/2018 | Wukovits et al. |
| 2018/0123443 | A1 | 5/2018 | Sreenivas et al. |
| 2018/0323720 | A1 | 11/2018 | Njiende et al. |

FOREIGN PATENT DOCUMENTS

| | | |
|---|---|---|
| TW | 200427204 A | 12/2004 |
| TW | I236207 B | 7/2005 |
| TW | 201444243 A | 11/2014 |
| TW | I497886 B | 8/2015 |

OTHER PUBLICATIONS

Bing Lu Ed—Anonymous: "A novel control method for interleaved transition mode PFC", Applied Power Electronics Conference and Exposition, 2008. APEC 2008. Twenty-Third Annual IEEE, IEEE, Piscataway, NJ, USA, Feb. 24, 2008, pp. 697-701.

Chris Bridge et al: "Understanding Interleaved Boundary Conduction Mode PFC Converters", Fairchild Semiconductor Power Seminar 2008-2009, Dec. 31, 2009, XP055277250, http://www.mikrocontroller.net/attachm ent/122761/interleaved_bcm_pfc.pdf.

Extended European Search Report for EP Application No. 21190243.2, dated Jan. 28, 2022; 5 pages.

Hangseok Choi et al: "A Cross-Coupled Master Slave Interleaving Method for Boundary Conduction Mode (BCM) PFC Converters", IEEE Transactions On Power Electronics, vol. 27, No. 10, Oct. 1, 2012, pp. 4202-4211.

Multimode Controller for SMPS, L6566BH; STMicroelectronics, Apr. 2012, 51 pages.

Power Factor Corrector; L6561; STMicroelectronics; 13 pages.

Quasi-Resonant SMPS Controller, L6565; STMicroelectronics, Jan. 2003, 17 pages.

TEA1507; GreenChip II SMPS control IC, Philips, Dec. 2000, 20 pages.

UCC28600 8-Pin Quasi-Resonant Flyback Green-Mode Controller, SLUS656K, Texas Instruments, Aug. 2015, 45 pages.

* cited by examiner

MULTI-PHASE SWITCHED-MODE POWER SUPPLIES

CROSS-REFERENCE TO RELATED APPLICATIONS

This application claims the benefit of and priority to U.S. application Ser. No. 17/007,862, filed Aug. 31, 2020. The entire disclosure of the above application is incorporated herein by reference.

FIELD

The present disclosure relates to multi-phase switched-mode power supplies, and particularly critically discontinuous multi-phase switched-mode power supplies.

BACKGROUND

This section provides background information related to the present disclosure which is not necessarily prior art.

Many customers are requiring power supplies to have a titanium-rated efficiency or higher, so the use of soft-switching power topologies is becoming more popular, such as the critically discontinuous mode for a front-end power factor correction (PFC) circuit. In order to reduce high peak currents that limit maximum output power, interleaved multi-phase operation is used.

Interleaved operation provides good ripple cancellation in the output voltage, but interleaving critically discontinuous mode circuits is difficult because the difference in switching frequencies between phases inhibits synchronization due to the zero current detection function of the critically discontinuous mode of operation.

SUMMARY

This section provides a general summary of the disclosure, and is not a comprehensive disclosure of its full scope or all of its features.

According to one aspect of the present disclosure, a multi-phase switched-mode power supply includes a pair of input terminals for receiving an alternating current (AC) or direct current (DC) voltage input from an input power source, a pair of output terminals for supplying a direct current (DC) voltage output to a load, and a first phase circuit coupled between the pair of input terminals and the pair of output terminals. The first phase circuit includes a first inductor coupled with a first switch. The power supply also includes a second phase circuit interleaved with the first phase circuit between the pair of input terminals and the pair of output terminals. The second phase circuit includes a second inductor coupled with a second switch. The power supply further includes a control circuit configured to output a first PWM signal to the first switch, and output a second PWM signal to the second switch. An on time of the second PWM signal is equal to an on time of the first PWM signal plus a fixed offset time period. The control circuit is configured to determine a period between at least two rising edges of the first PWM signal, determine an off trigger PWM signal according to the determined period, and change the second PWM signal to a logical low value when a falling edge of the off trigger PWM signal occurs while the second PWM signal has a logical high value.

According to another aspect of the present disclosure, a method controlling a multi-phase power supply is disclosed. The power supply includes a pair of input terminals for receiving an alternating current (AC) or direct current (DC) voltage input from an input power source, a pair of output terminals for supplying a direct current (DC) voltage output to a load, a first phase circuit coupled between the pair of input terminals and the pair of output terminals and including a first inductor coupled with a first switch, and a second phase circuit interleaved with the first phase circuit between the pair of input terminals and the pair of output terminals and including a second inductor coupled with a second switch. The method includes outputting a first PWM signal to the first switch, and outputting a second PWM signal to the second switch. An on time of the second PWM signal is equal to an on time of the first PWM signal plus a fixed offset time period. The method also includes determining a period between at least two rising edges of the first PWM signal, determining an off trigger PWM signal according to the determined period, an changing the second PWM signal to a logical low value when a falling edge of the off trigger PWM signal occurs while the second PWM signal has a logical high value.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts or features throughout the several views of the drawings.

DETAILED DESCRIPTION

Figure 1:
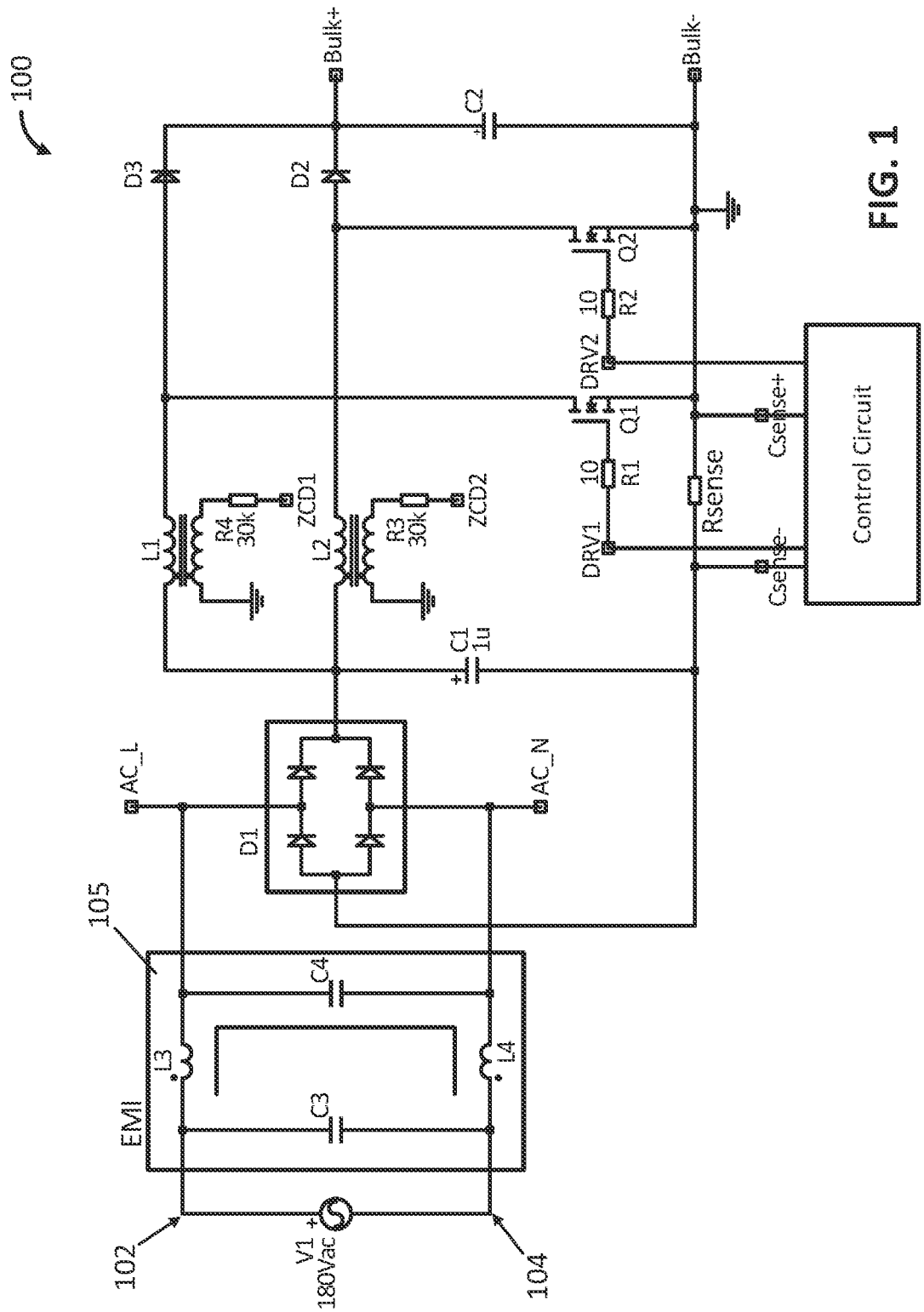
FIG. 1 is a circuit diagram of a multi-phase switched-mode power supply, according to one example embodiment of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

A multi-phase switched-mode power supply is illustrated in FIG. 1, and indicated generally by reference number 100. The system 100 includes a pair of input terminals 102 and 104 for receiving an alternating current (AC) or direct current (DC) voltage input from an input power source V1, and a pair of output terminals Bulk+ and Bulk− for supplying a direct current (DC) voltage output to a load (not shown in FIG. 1). Although FIG. 1 illustrates an AC voltage input of 180V, other embodiments may receive DC voltage inputs, AC voltage inputs having lesser or greater voltages, etc.

The power supply 100 includes a first phase circuit coupled between the pair of input terminals 102, 104 and the pair of output terminals Bulk+, Bulk−. The first phase circuit includes an inductor L1 coupled with a switch Q1.

The power supply 100 also includes a second phase circuit interleaved with the first phase circuit between the pair of input terminals 102, 104 and the pair of output terminals Bulk+, Bulk−. The second phase circuit includes an inductor L2 coupled with a switch Q2.

A control circuit 106 is configured to output a PWM signal DRV1 to the first switch Q1, and output a PWM signal DRV2 to the switch Q2. An on time of the PWM signal DRV2 is equal to an on time of the PWM signal DRV1 plus a fixed offset time period.

As explained further below, the control circuit 106 is configured to determine a period between at least two rising edges of the PWM signal DRV1, determine an off trigger PWM signal according to the determined period, and change the PWM signal DRV2 to a logical low value when a falling edge of the off trigger PWM signal occurs while the PWM signal DRV2 has a logical high value.

Figure 2:
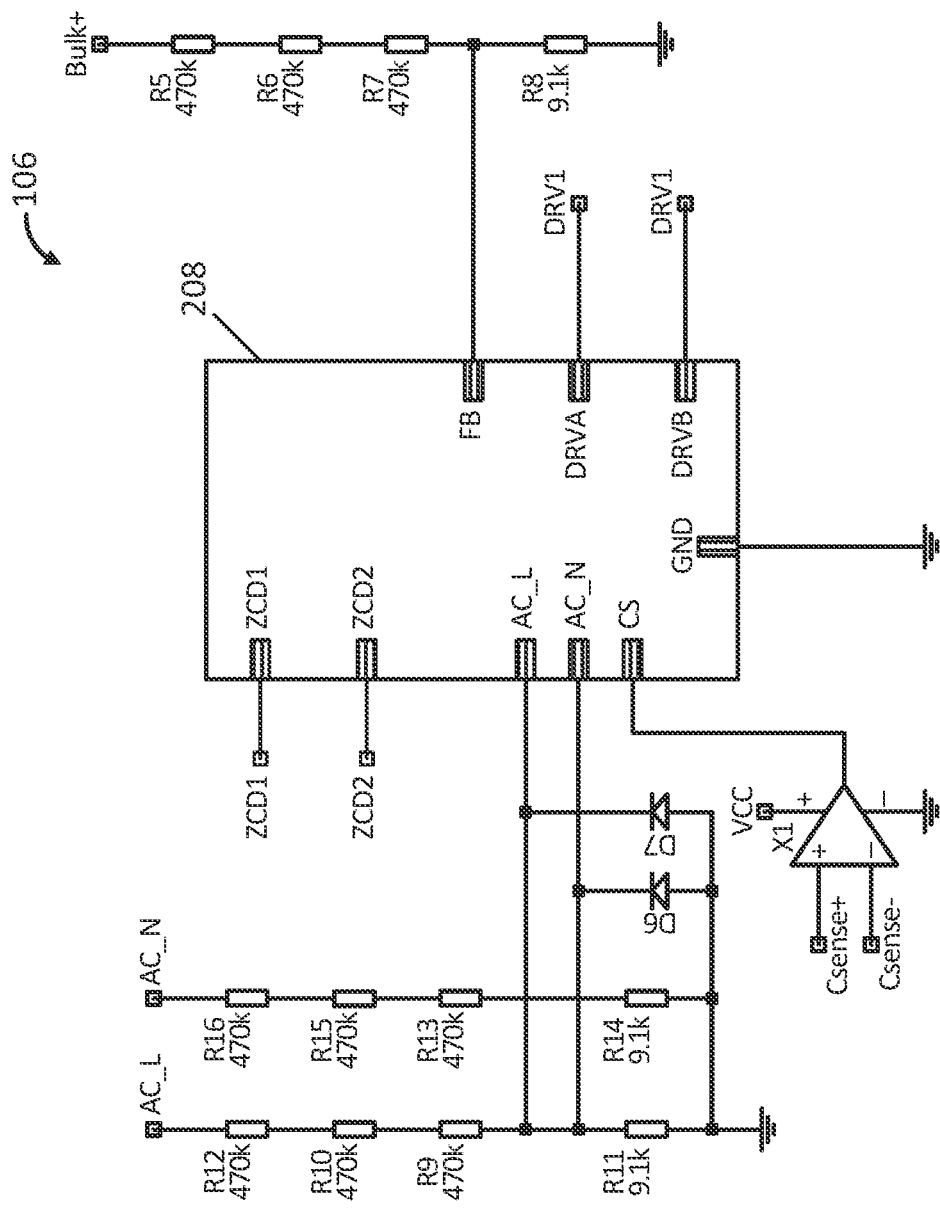
FIG. 2 is circuit diagram of an example control circuit wiring for the power supply of FIG. 1.

FIG. 2 illustrates an example wiring diagram of portions of the control circuit 106. As shown in FIG. 2, a digital controller 208 includes a zero current detection input ZCD1 coupled with the inductor L1 to detect a zero current crossing at the inductor L1, and a zero current detection input ZCD2 coupled with the inductor L2 to detect a zero current crossing at the inductor L2. FIG. 1 illustrates a resistor R4 coupled between the inductor L1 and the digital controller 208 to generate the signal ZCD1, and a resistor R3 coupled between the inductor L2 and the digital controller 208 to generate the signal ZCD1.

The digital controller 208 includes an AC line input AC_L and an AC neutral input AC_N. As shown in FIGS. 1 and 2, a voltage divider including the resistors R12, R10, R9 and R11 is coupled between the AC line input AC_L of the digital controller 208 and the line terminal 102 of the AC voltage input V1. A voltage divider including the resistors R16, R15, R13 and R14 is coupled between the AC neutral input AC_N of the digital controller 208 and the neutral terminal 104 of the AC voltage input V1. A diode D6 is coupled between the AC neutral input AC_N of the digital controller 208 and a circuit ground, and a diode D7 is coupled between the AC line input AC_L of the digital controller 208 and the circuit ground.

A current sense input CS of the digital controller is coupled to receive a signal from the amplifier X1, which amplifies the sensed differential current Csense+ and Csense− to determine a current through the current sense resistor Rsense shown in FIG. 1.

The controller 208 includes a feedback input FB for receiving the voltage output of the power supply 100. As shown in FIG. 2, a voltage divider including the resistors R5, R6, R7 and R8 is coupled between the output terminal Bulk+ and the feedback input FB. The example resistor values illustrated in FIGS. 1 and 2 are for purposes of illustration only, and other embodiments may use other suitable resistor values, may have more or less resistors, may have resistors coupled in other circuit arrangements, etc.

The digital controller 208 also includes a control signal output DRVA for supplying the PWM signal DRV1 to the switch Q1, a control signal output DRVB for supplying the PWM signal DRV2 to the switch Q2, and a ground input coupled to the circuit ground. Although FIG. 2 illustrates one particular connection interface between the digital controller 208 and other elements of the power supply 100, other embodiments may use different connection arrangements while implementing example control methods described herein.

Figure 3:
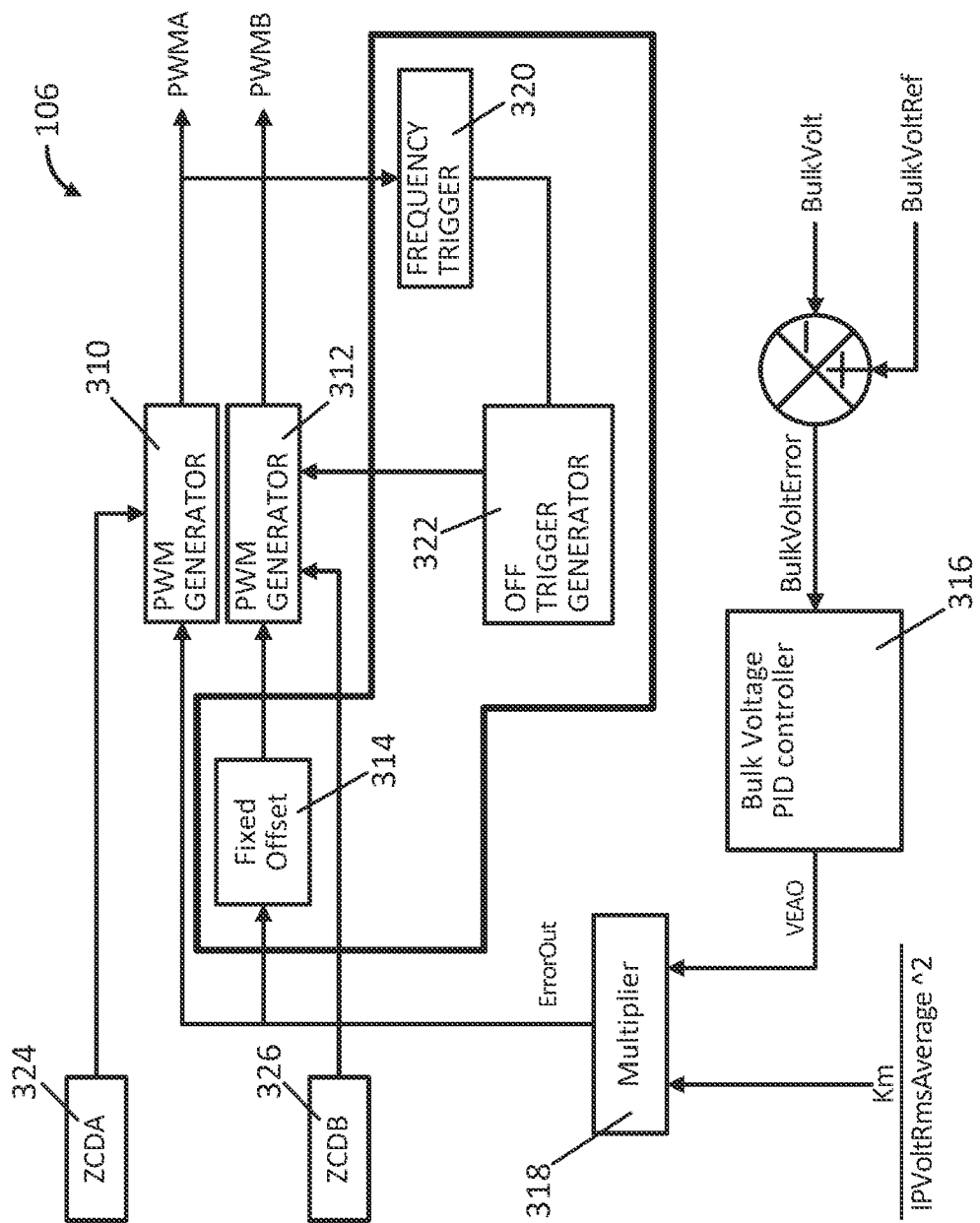
FIG. 3 is a block diagram example control circuit components for the power supply of FIG. 1.

FIG. 3 illustrates a block diagram showing example components of the control circuit 106. As shown in FIG. 3, the control circuit 106 includes a PWM generator circuit 310 to generate a pulse-width modulation (PWM) signal PWMA, and a PWM generator circuit 312 to generate the PWM signal PWMB. The signal PWMA may define the signal DRV1 supplied to the switch Q1, and the signal PWMB may define the signal supplied to the switch Q2.

The control circuit 106 includes a fixed offset circuit 314 coupled to and input of the PWM generator circuit 310 to add the fixed offset time period to the on time of the signal PWMB. For example, the control circuit 106 includes a voltage error amplifier 316 coupled to compare the DC voltage output (BulkVolt) to a voltage reference (BulkVoltRef). The fixed offset circuit 314 is coupled to receive a combined signal (via the multiplier circuit 318) from an output of the voltage error amplifier 316 and an equivalent root mean square (RMS) voltage of the AC voltage input. The fixed offset time period may be a constant value which only requires one time trimming depending on the speed of phase adjustment. In some embodiments, the fixed offset circuit 314 may include a hardware delay that replicates the function of adding additional on time via software.

As shown in FIG. 3, a frequency capture circuit 320 is coupled to determine the period between at least two rising edges of the signal PWMA. The frequency capture circuit 320 may include a digital timer or an analog voltage ramp for measuring an instantaneous voltage of the signal PWMA. In some embodiments, the frequency capture circuit 320 may determine the period between at least two rising edges of the signal PWMA by measuring an average value of multiple cycles of the signal PWMA, by predicting a next cycle of the signal PWMA according to the voltage input, the voltage output and a latest duty cycle of the signal PWMA, etc.

The control circuit 106 also includes an off trigger generator circuit 322 coupled between the frequency capture circuit 320 and the PWM generator circuit 312. The off trigger generator circuit 322 may be configured to generate an off trigger PWM signal with a 180 degree phase shift from the signal PWMA, by using one half of the determined period between the at least two rising edges of the signal PWMA, one half of the measured average value of the multiple cycles of the signal PWMA, one half of the predicted next cycle of the signal PWMA, etc. In some embodiments, an on time of the off trigger PWM signal may be equal to the on time of the signal PWMA.

As shown in FIG. 3, the control circuit 106 includes a zero current detector (ZCD) circuit 324 coupled with the PWM generator circuit 310, for detecting a zero current crossing at the inductor L1. A ZCD circuit 326 is coupled with the PWM generator circuit 312 to detect a zero current crossing at the inductor L2. Although FIG. 3 illustrates one particular arrangement of the components outside of the highlighted portion (e.g., the fixed offset circuit 314, the frequency capture circuit 320 and the off trigger generator circuit 322) of the control circuit 106 for performing example control methods described herein, in other embodiments the components may be arranged differently while the highlighted portion of the control circuit 106 performs example control methods described herein.

Example control methods described herein (e.g., as performed by the control circuit 106, etc.), may use zero current detection for each inductor L1 and L2 (e.g., each PFC choke), to allow the inductor to reset on its own. Each inductor L1 and L2 will reset at different times depending on the inductance, gate drive delay, instantaneous input voltage, and instantaneous output voltage. Due to the different reset timing, the switching frequency may be different for each phase.

Some prior art control methods that only detect one phase and force the second phase to be out-of-phase at a certain phase angle depending of the number of phases (e.g., for 2-phase operation, the second phase is forced to be 180 degrees out of phase), may not allow the second phase to achieve valley switching or full reset, especially if the inductance is large (e.g., the power supply mostly operates at low frequency). Some prior art control methods that use ZCD detection for each inductor measure the frequency of both phases to keep them equal by adjusting the on time of one phase or both phases, and the control method sets the phase shift of the other phase(s). In contrast, example control methods described herein may only measure the switching period of the main phase, and provide a fixed turn off point for the second phase (e.g., according to the on time and the period of the main phase).

Also, example control methods described herein may add a fixed additional on time for the other phases to allow the current reset point to shift to the right by operating at a lower frequency. The second phase is allowed to slowly shift on its own to a correct phase angle, until it reaches the turn off trigger point to fix the second phase in place. In order to fix the second phase in place, the on time is cut off due to the turn off trigger (e.g., from the off trigger generator circuit 322, etc.), which in reduces the switching period until both frequencies are the same (e.g., the switching frequency of each switch Q1 and Q2 is equal). In view of the above, the phase control may not require any complex calculation, such as implementing error calculation, etc. Each phase of the power supply 100 may adjust its phase on its own.

Some prior art control methods use the rising or falling edge of a PWM signal, average across multiple cycles, and compare the average to a fixed reference to control the phase angle shift. This creates a higher processing requirement for the controller, especially for multi-phase operation where complex calculations are performed to provide the phase control for each individual phase. In contrast, example control methods described herein may not require any complex calculations for multi-phase operation. As described above, a fixed turn off trigger is generated (e.g., based on the period of the main phase), and applied to each individual phase. Accordingly, each phase of the power supply may adjust its timing on its own, which reduces the hardware requirement for the controller.

Referring again to FIG. 1, the power supply 100 optionally includes a power factor correction (PFC) circuit coupled between the pair of input terminals 102, 104 and the first and second phase circuits. The PFC circuit includes an electromagnetic interference (EMI) filter circuit 105. The EMI filter circuit 105 may include two inductors L3 and L4, two capacitors C3 and C4, more or less inductors, more or less capacitors, etc. The PFC circuit also includes a bridge circuit D1 including four diodes.

Although FIG. 1 illustrates the power supply 100 as including an AC voltage input and a PFC circuit with an EMI filter circuit 105 and a bridge circuit D1 for AC-DC power conversion, other embodiments may include other suitable PFC circuits, other embodiments may be DC-DC converters that receive a DC voltage input, etc. For example, the power supply 100 may use any suitable AC-DC or DC-DC converter topology, such as a buck converter topology, a boost converter topology, or a forward converter topology, etc. The power supply 100 may use variable frequency operations, interleaved operation, etc.

In some embodiments, the power supply 100 may include more than two interleaved phase circuits (e.g., three phases, four phases, etc.). Each phase circuit may include its own inductor and switch, and the control circuit 106 may generate PWM signals for each switch, with a separate off trigger PWM signal for each switch other than the switch of the first phase circuit.

As shown in FIG. 1, the power supply 100 may include an output capacitor C2 coupled between the pair of output terminals Bulk+ and Bulk−, a diode D3 coupled between the inductor L1 and the output terminal Bulk+, a diode D2 coupled between the inductor L2 and the output terminal Bulk+, and a capacitor C1 coupled with the inductors L1 and L2. In other embodiments, the power supply 100 may include more or less capacitors and diodes, capacitors and diodes coupled in other arrangements, etc. The terminals 102, 104, Bulk+ and Bulk− may include any suitable electrical terminal, wire, circuit trace, etc., for receiving a voltage input from a voltage source or supplying a voltage output to a load.

The control circuit 106 may be configured to control switching operation of the switches Q1 and Q2 to operate the power supply 100 in any suitable mode of operation, such as in a quasi-resonant mode of operation, a critically discontinuous mode of operation, etc.

The control circuit 106 and the digital controller 208 may include any suitable microprocessor, microcontroller, integrated circuit, digital signal processor, etc., which may include memory. The control circuit 106 and the digital controller 208 may be configured to perform (e.g., operable to perform, etc.) any of the example processes described herein using any suitable hardware and/or software implementation. For example, the control circuit 106 and the digital controller 208 may execute computer-executable instructions stored in a memory, may include one or more logic gates, control circuitry, etc., as described above.

Figure 4:
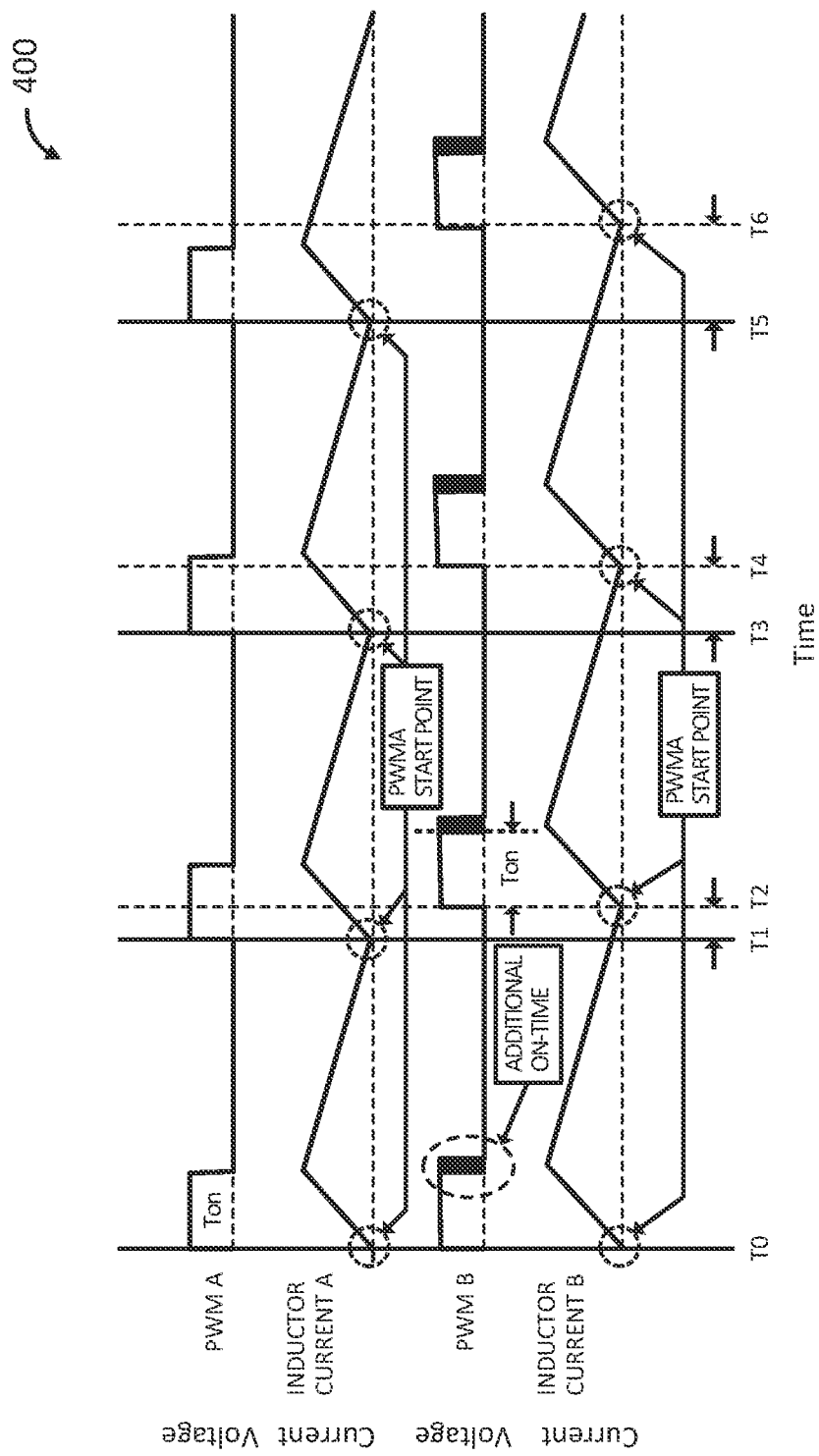
FIG. 4 is an illustration of waveforms showing example PWM control signals and inductor currents of the power supply of FIG. 1.

FIG. 4 illustrates example waveforms 400 showing the control signals PWMA and PWMB, and the inductor current A and inductor current B, during multiple switching cycles of the power supply 100. For example, the control signal PWMA may be supplied to the switch Q1 of FIG. 1 and the control signal PWMB may be supplied to the switch Q2 of FIG. 1. The inductor current A may represent a current through the inductor L1, and the inductor current B may represent a current through the inductor L2.

As shown in FIG. 4, the control signal PWMA has an on time Ton, and the control signal PWMB has an on time that is equal to Ton plus a fixed offset of additional on time. At time T0, both of the control signals PWMA and PWMB go to a logical high value, and the inductor currents A and B ramp up. Because the control signal PWMB has a longer on time than the control signal PWMA due to the fixed offset, the inductor current B ramps up to a higher value than the inductor current A before the control signal PWMB transitions to a logical low value. Although FIG. 4 illustrates adding additional on time to the control signal PWMB, in other embodiments the control method may be implemented by reducing the on time of the control signal PWMA.

At time T1, the inductor current A reaches a zero value, and the control signal PWMA goes to a logical high value again (e.g., due to the ZCD1 signal triggering the PWM generator 310 in FIG. 3, etc.). The inductor current B is not yet zero at time T1, so the control signal PWMB does not go to a logical high value until time T2 (e.g., based on the ZCD2 signal triggering the PWM generator 312 when the inductor current B reaches zero at time T2, etc.).

The process continues again at time T3, where the control signal PWMA goes to a logical high value due to the zero current condition of the inductor current A, while the control signal PWMB does not go to a logical high value until the time T4 where the inductor current B reaches a zero current condition. As shown in FIG. 4, the delay between times T3 and T4 is greater than the delay between times T2 and T1, due to the offset value added to the on time of the control signal PWMB.

The delay between the rising edges of the control signals PWMA and PWMB is further increased at times T5 and T6. Again, the offset value added to the control signal PWMB continually causes the inductor current B to ramp up higher than the inductor current A, and therefore extends the time for the inductor current B to reach relative to the inductor current A more and more each cycle.

Figure 5:
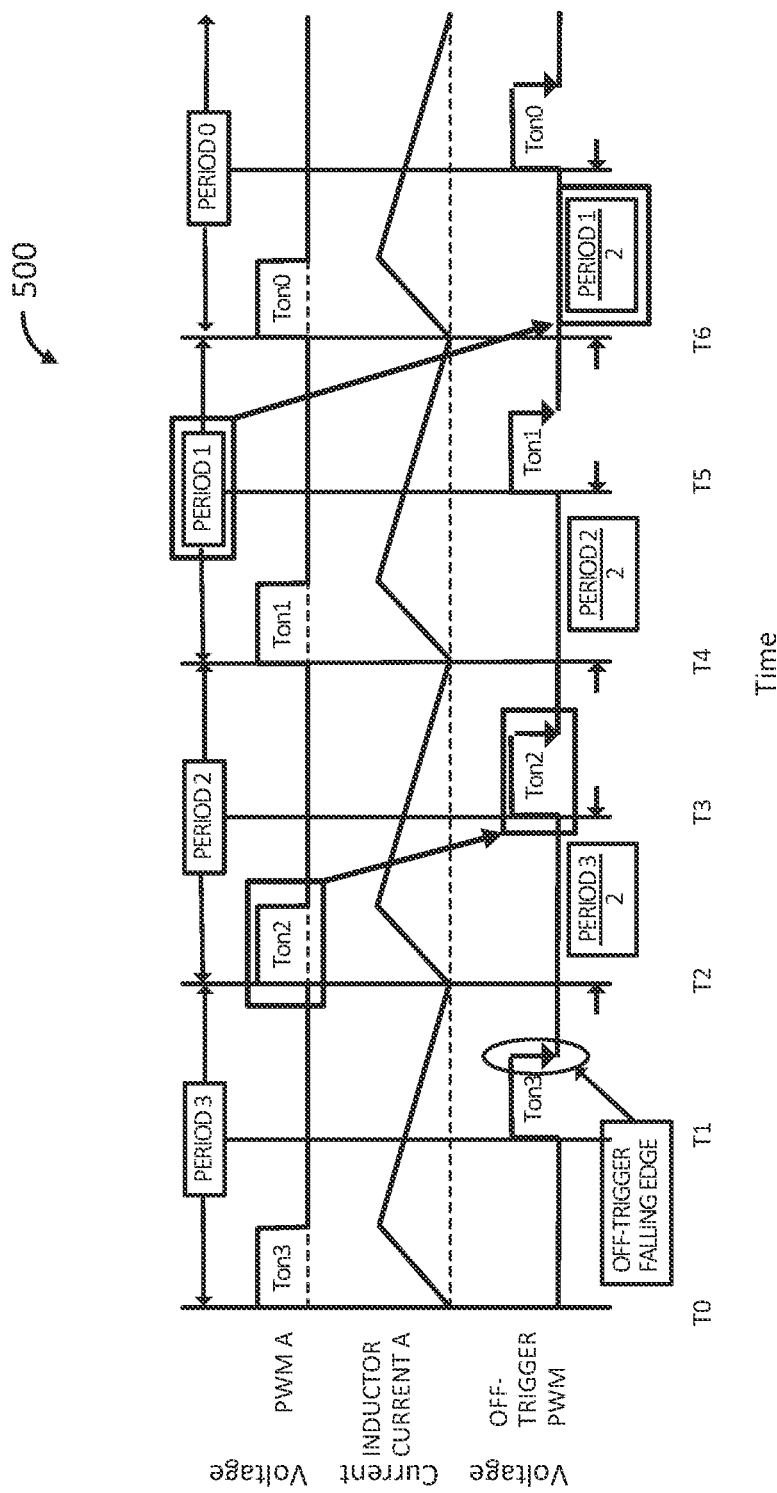
FIG. 5 is an illustration of waveforms showing an example off trigger PWM signal of the power supply of FIG. 1.

FIG. 5 illustrates example waveforms 500 showing how to determine the off trigger PWM signal based on the control signal PWMA, along with the inductor current A. As shown in FIG. 5, periods between rising edges of the control signal PWMA are first determined. For example, PERIOD3 identifies a time period between rising edges of the pulse Ton3 at time T0 and the pulse Ton2 at time T2, PERIOD2 identifies a period between rising edges of the pulse Ton2 at time T2 and the pulse Ton1 at time T4, and PERIOD1 identifies a period between rising edges of the pulse Ton1 at time T4 and the pulse Ton0 at time T6.

As shown in FIG. 5, each pulse of the off trigger PWM signal starts at a 180 degree opposite phase of the pulses of the control signal PWMA. For example, each pulse of the off trigger PWM signal may start halfway through the determined period between pulses of the control signal PWMA.

FIG. 5 illustrates a rising edge of the pulse Ton3 of the off trigger PWM signal starting at time T1, which is the midpoint of the determined time period PERIOD3 between pulses of the control signal PWMA. Similarly, the rising edge of the pulse Ton2 of the off trigger PWM signal occurs at T3, which is to the time T2 plus a delay of the prior time period PERIOD3 divided by two. The rising edge of the pulse Ton1 of the off trigger PWM signal occurs at T5, which is to the time T4 plus a delay of the prior time period PERIOD2 divided by two. The rising edge of the pulse Ton0 of the off trigger PWM signal occurs at T7, which is to the time T6 plus a delay of the prior time period PERIOD1 divided by two.

The on time of each pulse of the off trigger PWM signal may be equal to the on time of each pulse of the control signal PWMA. FIG. 5 also illustrates falling edges of the pulses of the off trigger PWM signal, which may be used to turn off the control signal PWMB early as described further below.

Figure 6:
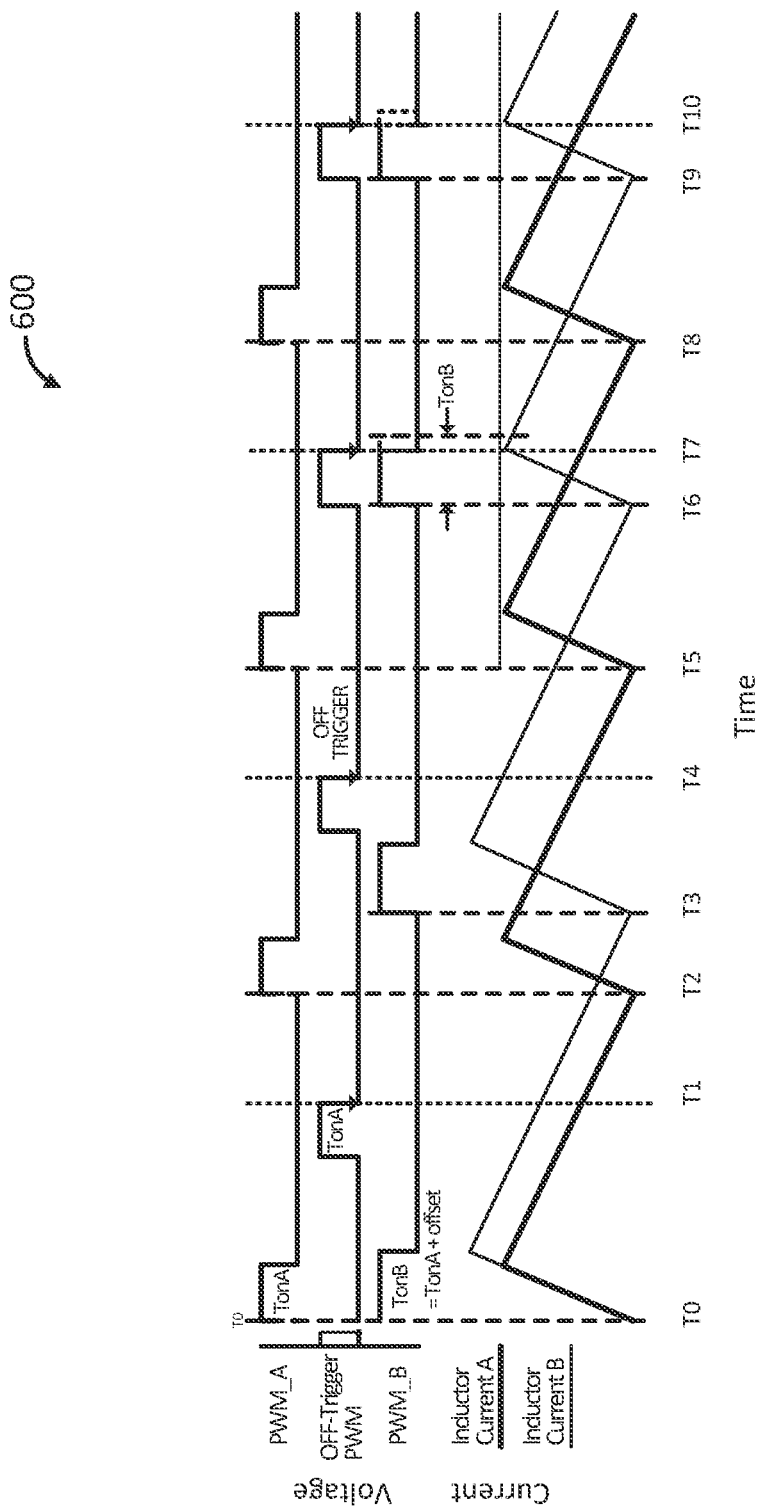
FIG. 6 is an illustration of waveforms showing examples PWM control signals, inductor currents and an off trigger PWM signal for multiple cycles of the power supply of FIG. 1.

FIG. 6 illustrates example waveforms 600 showing the interaction of the off trigger PWM signal with the control signals PWMA and PWMB, and the inductor currents A and B. As shown in FIG. 6, at time T0, pulses of both control signals PWMA and PWMB start at the same time.

At time T1, a falling edge of the off trigger PWM signal occurs. Because the control signal PWMB is at a logical low value at time T1, the control signal PWMB is not affected. At time T2, the control signal PWMA goes to a logical high value in response to a zero current condition of the inductor current A, while the control signal PWMB does not go to a logical high value until time T3 (e.g., because the inductor current B does not reach a zero current condition until time T3 due to the offset added to the on time of the control signal PWMB, etc.).

At time T4, a falling edge of the off trigger PWM signal again occurs. Because the control signal PWMB is at a logical low value at time T4, the control signal PWMB is not affected. At time T5, the control signal PWMA goes to a logical high value in response to a zero current condition of the inductor current A, while the control signal PWMB does not go to a logical high value until time T6 (e.g., because the inductor current B does not reach a zero current condition until time T6 due to the offset added to the on time of the control signal PWMB, etc.).

A falling edge of the off trigger PWM signal occurs at time T7, while the control signal PWMB is at a logical high level. This causes the control signal PWMB to transition to a logical low level early, at the same time T7 as the falling edge of the off trigger PWM signal, instead of the control signal PWMB staying at the logical high value until its normal period of TonB (e.g., TonA plus an offset) has ended.

The shortened on time of the control signal PWMB at time T7 reduces the ramp up of the inductor current B, which leads to a steady state condition where the inductor currents A and B are equal and opposite phase to one another. For example, at time T8 the control signal PWMA goes to a logical high value, and at time T9 both the off trigger PWM signal and the control signal PWMB go to logical high values. The falling edge of the off trigger PWM signal at time T10 cuts short the control signal PWMB again, to maintain the steady state operation of the inductor currents A and B.

In view of the above, the offset value and the off trigger PWM signal allow the power supply 100 to start off with the control signals PWMA and PWMB starting at the same time, while continually adjusting the control signal PWMB over subsequent cycles according to the off trigger PWM signal, in order to reach and maintain a steady state operation of the inductor currents A and B as balanced and opposite phases to one another. Similarly, if the timing or inductor currents A and B are disturbed during operation of the power supply 100, the control signal PWMB may be again adjusted over subsequent cycles according to the off trigger PWM signal, in order to again reach and maintain a steady state operation of the inductor currents A and B as balanced and opposite phases to one another.

In some embodiments, an inductance of the inductor L1 may be lower (or higher) than the inductance of the inductor L2. With DC input, the switching frequency of the switches Q1 and Q2 may be the same. However, when using fast PFC average mode control where the inductor L1 has a lower inductance, the switching frequency may be different where the second phase operates at a lower frequency. This may result in a similar function as illustrated in FIG. 6, and adding the off trigger signal provides phase control for the different phases.

As another option, when using peak current mode control where the inductor L1 has a lower inductance than the inductor L2, the switching frequency may again be different where the second phase operates at a lower frequency. Peak current control may compare the sensed inductor current with the output of a compensator for PFC operation. This may result in a similar function as illustrated in FIG. 6, and adding the off trigger signal provides phase control for the different phases.

Figure 7:
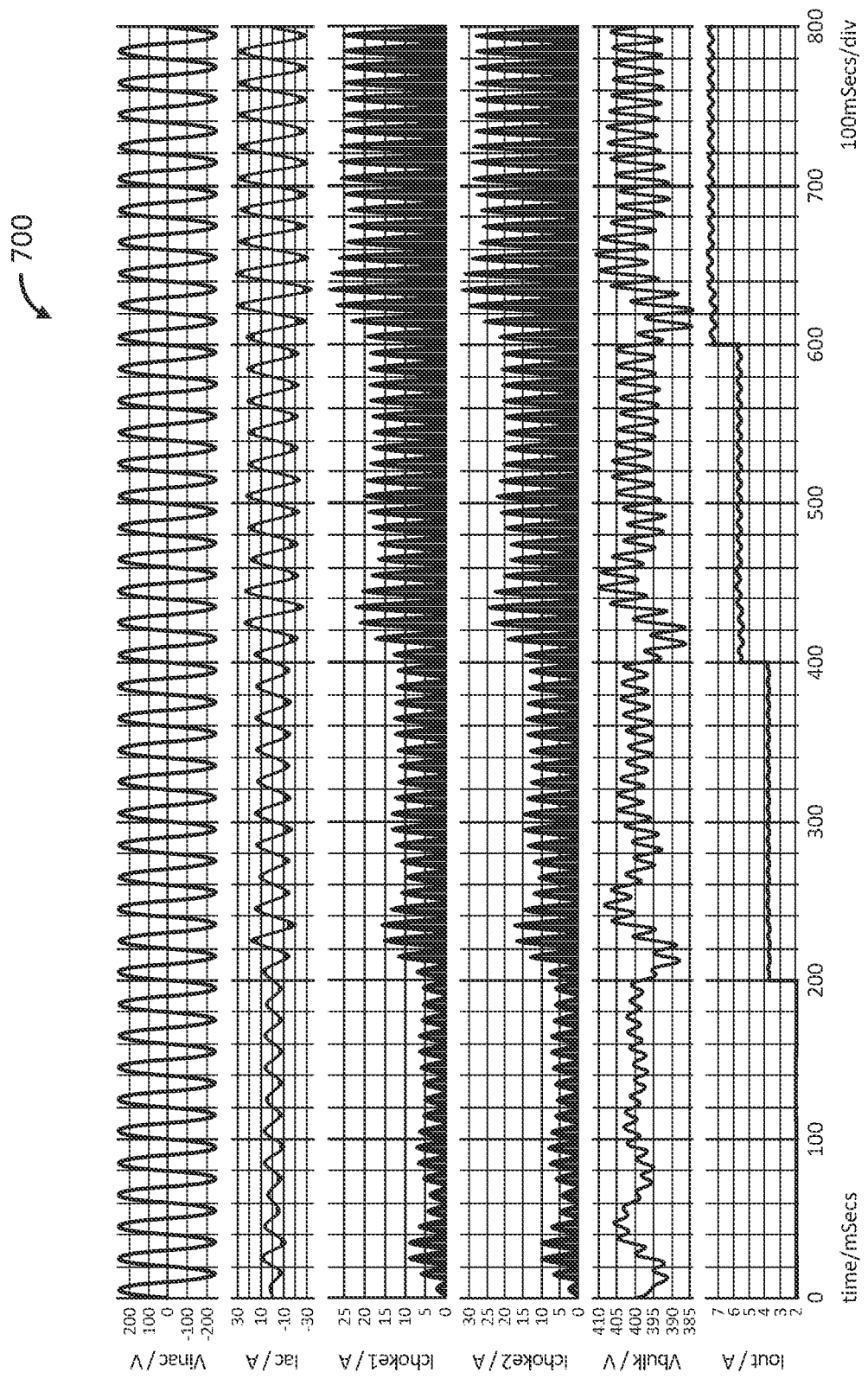
FIG. 7 is an illustration of waveforms showing example input and output voltages and currents for the power supply of FIG. 1.

FIG. 7 illustrates example waveforms 700 showing currents and voltages of different components of the power supply 100 during four different load conditions. Specifically, FIG. 7 illustrates an AC voltage input VinAC, an input current Iac, a current Ichoke1 through the inductor L1, a current Ichoke2 through the inductor L2, a voltage output Vbulk, and an output current Iout.

A first load condition is illustrated from zero to 200 milliseconds, at an output current of about two Amps. A second load condition is illustrated from 200 to 400 milliseconds at an output current of about four Amps, a third load condition is illustrated from 400 to 600 milliseconds at an output current of about 5.5 Amps, and a fourth load condition is illustrated from 600 to 800 milliseconds, at an output current of about 7.5 Amps.

Figure 8:
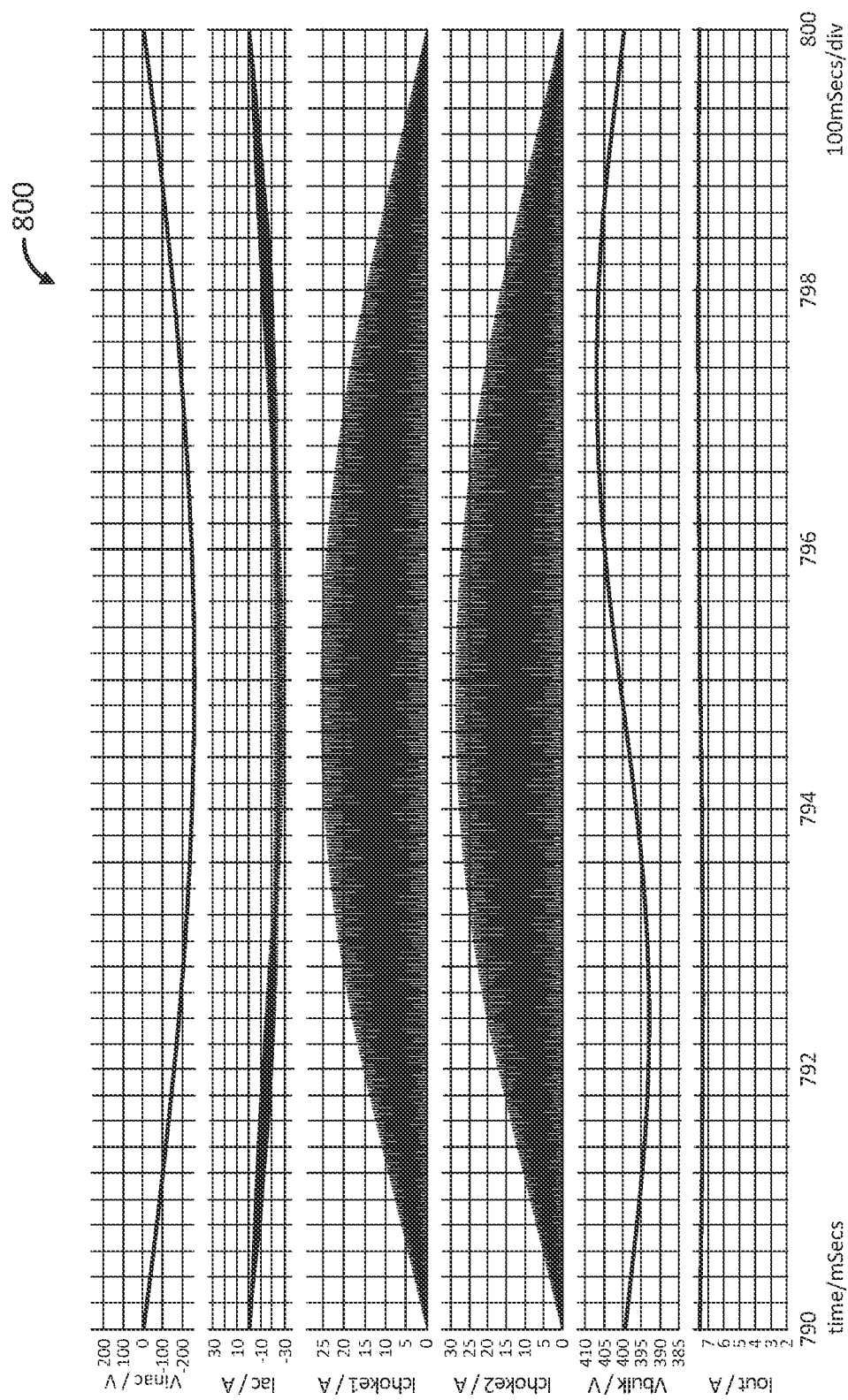
FIG. 8 is an illustration of waveforms showing example showing example input and output voltages and currents for the power supply of FIG. 1 during one cycle.
Figure 9:
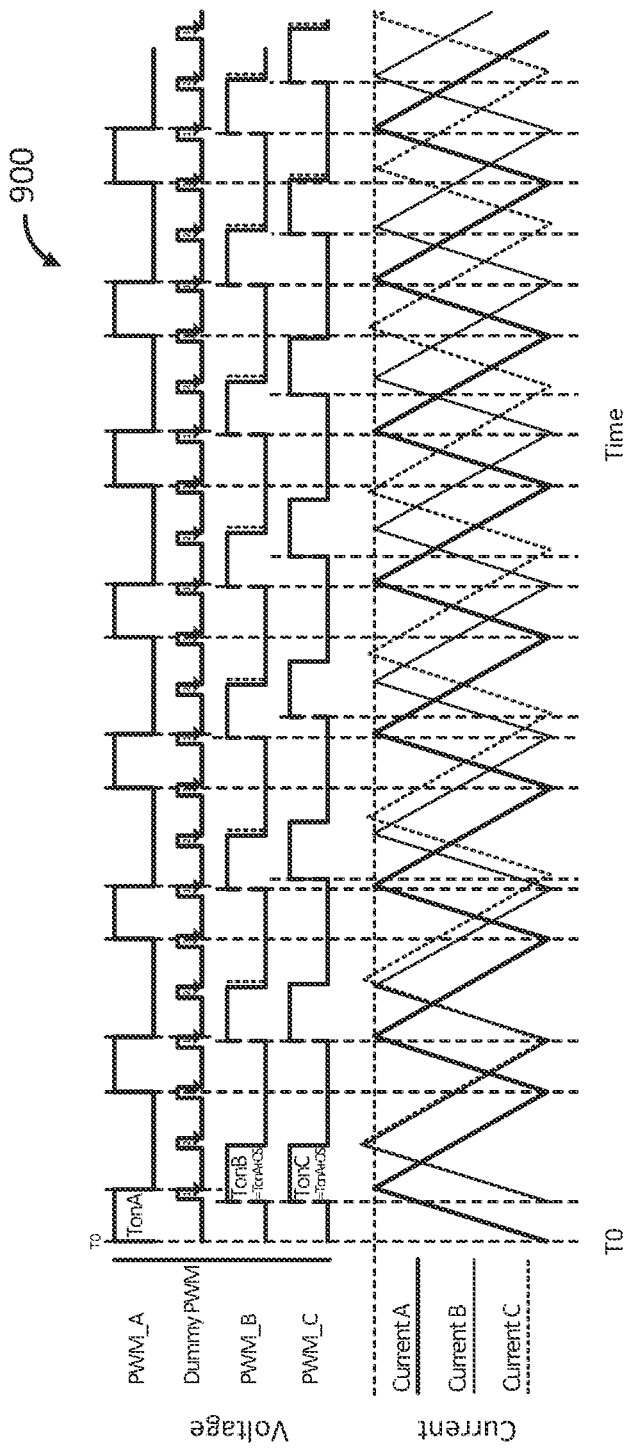
FIG. 9 is an illustration of waveforms showing example PWM control signals and inductor currents for a three-phase switched-mode power supply, according to another example embodiment of the present disclosure.

FIG. 8 illustrates example waveforms 800 showing currents and voltages of different components of the power supply 100 based on a 100% load condition for a one-half cycle of the AC voltage input. As shown in FIG. 8, ripple cancellation is most effective when the current of the inductor L1 is 180 degrees out of phase with respect to the current though the inductor L2. FIGS. 7 and 8 also illustrate the effectiveness of using the phase control techniques described herein for different stepped load conditions. FIG. 9 illustrates example waveforms 900 showing PWM control signals and inductor currents for a three phase power supply. For example, a control signal PWMA is supplied to a switch of a first phase circuit of the power supply, where the current A corresponds to a current through an inductor of the first phase circuit.

A control signal PWMB is supplied to a switch of a second phase circuit of the power supply, where the current B corresponds to a current through an inductor of the second phase circuit. A control signal PWMC is supplied to a switch of a third phase circuit of the power supply, where the current C corresponds to a current through an inductor of the third phase circuit.

As shown in FIG. 9, a control signal DummyPWM has a frequency that is equal to double the frequency of a previous period of the control signal PWMA. The control signal DummyPWM has a duty cycle of ten percent. Each of the control signals PWMB and PWMC have an on time that is equal to an on time of the control signal PWMA plus a fixed offset.

The off trigger for each phase PWMB and PWMC will have a different shift. For example, the pseudo-code illustrated in FIG. 9 describes the off trigger for the signal PWMB as adding 33% of the previous period of the control signal PWMA to the start of a pulse of the control signal PWMA, and the off trigger for the signal PWMC as adding 66% of the previous period of the control signal PWMA to the start of a pulse of the control signal PWMA.

As shown in FIG. 9, the inductor currents A, B and C of the three phases reach a steady state balance after multiple cycles. The control signals PWMB and PWMC start out with a phase difference of ninety degrees relative to the control signal PWMA at time T0, although in other embodiments the control signals may all start at the same time, may start with different phase offsets, etc.

In another example embodiment, a method controlling a multi-phase power supply is disclosed. The power supply includes a pair of input terminals for receiving an alternating current (AC) or direct current (DC) voltage input from an input power source, a pair of output terminals for supplying a direct current (DC) voltage output to a load, a first phase circuit coupled between the pair of input terminals and the pair of output terminals and including a first inductor coupled with a first switch, and a second phase circuit interleaved with the first phase circuit between the pair of input terminals and the pair of output terminals and including a second inductor coupled with a second switch.

The method includes outputting a first PWM signal to the first switch, and outputting a second PWM signal to the second switch. An on time of the second PWM signal is equal to an on time of the first PWM signal plus a fixed offset time period. The method also includes determining a period between at least two rising edges of the first PWM signal, determining an off trigger PWM signal according to the determined period, an changing the second PWM signal to a logical low value when a falling edge of the off trigger PWM signal occurs while the second PWM signal has a logical high value.

Determining the period between the at least two rising edges of the first PWM signal may include measuring the period using a digital timer or an analog voltage ramp for measuring an instantaneous voltage of the first PWM signal. Generating the off trigger PWM signal may include generating the off trigger PWM signal with a 180 degree phase shift from the first PWM signal by using one half of the determined period between the two rising edges of the first PWM signal.

In some embodiments, determining the period between the at least two rising edges of the first PWM signal may include measuring an average value of multiple cycles of the first PWM signal or by predicting a next cycle of the first PWM signal according to the voltage input, the voltage output and a latest duty cycle of the first PWM signal. Generating the off trigger PWM signal may include generating the off trigger PWM signal with a 180 degree phase shift from the first PWM signal by using one half of the measured average value of the multiple cycles of the first PWM signal or one half of the predicted next cycle of the first PWM signal. An on time of the off trigger PWM signal is equal to the on time of the first PWM signal.

The method may include initiating the first PWM signal and the second PWM signal at a same time during startup of the power supply, and continuing to change the second PWM signal until a switching period of first PWM signal is equal to a switching period of the second PWM signal. The method may include, in response to the switching periods of the first PWM signal and the second PWM signal being disturbed to become unequal, continuing to change the second PWM signal until the switching period of first PWM signal is again equal to the switching period of the second PWM signal.

Example embodiments described herein may provide one or more (or none) of the following advantages: simplicity of control circuit design and phase control method, lower processing requirements for the phase control when implemented with more than two phases (e.g., a four phase converter, etc.), use of a cheaper controller, ease of implementation due to a lack of need for compensation for phase control (especially for more than two phase applications). For example, in a four-phase converter, each phase may require independent compensation that can affect the stability of the overall converter.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A multi-phase switched-mode power supply, the power supply comprising:
a first phase circuit comprising a first switch;
a second phase circuit interleaved with the first phase circuit and comprising a second switch; and
a control circuit configured to:
output a first PWM signal to the first switch;
output a second PWM signal to the second switch, wherein an on time of the second PWM signal is equal to an on time of the first PWM signal plus a fixed offset time period;
determine a period between at least two rising edges of the first PWM signal;
determine an off trigger PWM signal according to the determined period; and
change the second PWM signal to a logical low value in response to a falling edge of the off trigger PWM signal occurring while the second PWM signal has a logical high value.

2. The power supply of claim 1, wherein the control circuit further comprises:
a first PWM generator circuit to generate the first PWM signal;
a second PWM generator circuit to generate the second PWM signal; and
a fixed offset circuit coupled to and input of the second PWM generator circuit to add the fixed offset time period to the on time of the second PWM signal.

3. The power supply of claim 2, wherein the control circuit further comprises a voltage error amplifier coupled to compare a DC voltage output of the power supply to a voltage reference; and
wherein the fixed offset circuit is coupled to receive a combined signal from an output of the voltage error amplifier and an equivalent root mean square (RMS) voltage of an AC voltage input of the power supply.

4. The power supply of claim 2, wherein the control circuit further comprises a frequency capture circuit to determine the period between the at least two rising edges of the first PWM signal; and
wherein the frequency capture circuit comprises a digital timer or an analog voltage ramp for measuring an instantaneous voltage of the first PWM signal.

5. The power supply of claim 4, wherein the control circuit further comprises an off trigger generator circuit coupled between the frequency capture circuit and the second PWM generator circuit; and
wherein the off trigger generator circuit is configured to generate the off trigger PWM signal with a 180-degree phase shift from the first PWM signal by using one half of the determined period between the at least two rising edges of the first PWM signal.

6. The power supply of claim 4, wherein:
the frequency capture circuit is configured to determine the period between the at least two rising edges of the first PWM signal by measuring an average value of multiple cycles of the first PWM signal or by predicting a next cycle of the first PWM signal based on a latest duty cycle of the first PWM signal;
the control circuit further comprises an off trigger generator circuit coupled between the frequency capture circuit and the second PWM generator circuit; and
the off trigger generator circuit is configured to generate the off trigger PWM signal with a 180 degree phase shift from the first PWM signal by using one half of the measured average value of the multiple cycles of the first PWM signal or one half of the predicted next cycle of the first PWM signal.

7. The power supply of claim 1, wherein an on time of the off trigger PWM signal is equal to the on time of the first PWM signal.

8. The power supply of claim 1, wherein the first phase circuit further comprises a first inductor coupled with the first switch;
wherein the second phase circuit further comprises a second inductor coupled with the second switch; and
wherein the control circuit comprises:
a first zero current detector (ZCD) circuit coupled between the first inductor and the first PWM generator circuit to detect a zero current crossing at the first inductor; and
a second ZCD circuit coupled between the second inductor and the second PWM generator circuit to detect a zero current crossing at the second inductor.

9. The power supply of claim 1, further comprising a third phase circuit interleaved with the first phase circuit and the second phase circuit, the third phase circuit comprising a third inductor coupled with a third switch.

10. The power supply of claim 1, further comprising a power factor correction (PFC) circuit coupled to the first and second phase circuits, the PFC circuit comprising:
an electromagnetic interference (EMI) filter circuit comprising at least two capacitors and at least two inductors; and
a bridge circuit comprising at least four diodes.

11. The power supply of claim 1, further comprising an output capacitor coupled between a pair of output terminals, a first diode coupled between the first phase circuit and a first one of the pair of output terminals, and a second diode coupled between the second phase circuit and the first one of the pair of output terminals.

12. The power supply of claim 1, wherein the control circuit is configured to initiate the first PWM signal and the second PWM signal at a same time during startup of the power supply, and continue changing the second PWM signal until a switching period of first PWM signal is equal to a switching period of the second PWM signal.

13. The power supply of claim 12, wherein the control circuit is configured to, in response to the switching periods of the first PWM signal and the second PWM signal being disturbed to become unequal, continue changing the second PWM signal until the switching period of first PWM signal is again equal to the switching period of the second PWM signal.

14. The power supply of claim 1, wherein the control circuit is configured to operate the first phase circuit and the second phase circuit in a quasi-resonant mode of operation or a critically discontinuous mode of operation.

15. A method of controlling a multi-phase power supply comprising:
outputting a first PWM signal to a first switch;
outputting a second PWM signal to a second switch, wherein an on time of the second PWM signal is equal to an on time of the first PWM signal plus a fixed offset time period;
determining a period between at least two rising edges of the first PWM signal;
determining an off trigger PWM signal according to the determined period; and
changing the second PWM signal to a logical low value in response to a falling edge of the off trigger PWM signal occurring while the second PWM signal has a logical high value.

16. The method of claim 15, wherein the multi-phase power supply comprises:
a first phase circuit comprising a first inductor coupled with a first switch; and
a second phase circuit interleaved with the first phase circuit and comprising a second inductor coupled with a second switch.

17. The method of claim 15, wherein determining the period between the at least two rising edges of the first PWM signal comprises measuring the period using a digital timer or an analog voltage ramp for measuring an instantaneous voltage of the first PWM signal.

18. The method of claim 17, wherein generating the off trigger PWM signal comprises generating the off trigger PWM signal with a 180-degree phase shift from the first PWM signal by using one half of the determined period between the two rising edges of the first PWM signal.

19. The method of claim 17, wherein:
determining the period between the at least two rising edges of the first PWM signal comprises measuring an average value of multiple cycles of the first PWM signal or by predicting a next cycle of the first PWM signal based on a latest duty cycle of the first PWM signal; and
generating the off trigger PWM signal comprises generating the off trigger PWM signal with a 180-degree phase shift from the first PWM signal by using one half of the measured average value of the multiple cycles of the first PWM signal or one half of the predicted next cycle of the first PWM signal.

20. The method of claim 15, wherein an on time of the off trigger PWM signal is equal to the on time of the first PWM signal.

* * * * *